June 13, 1939. K. RIESSELMANN Plant Pat. 330
ROSE
Filed Nov. 23, 1938
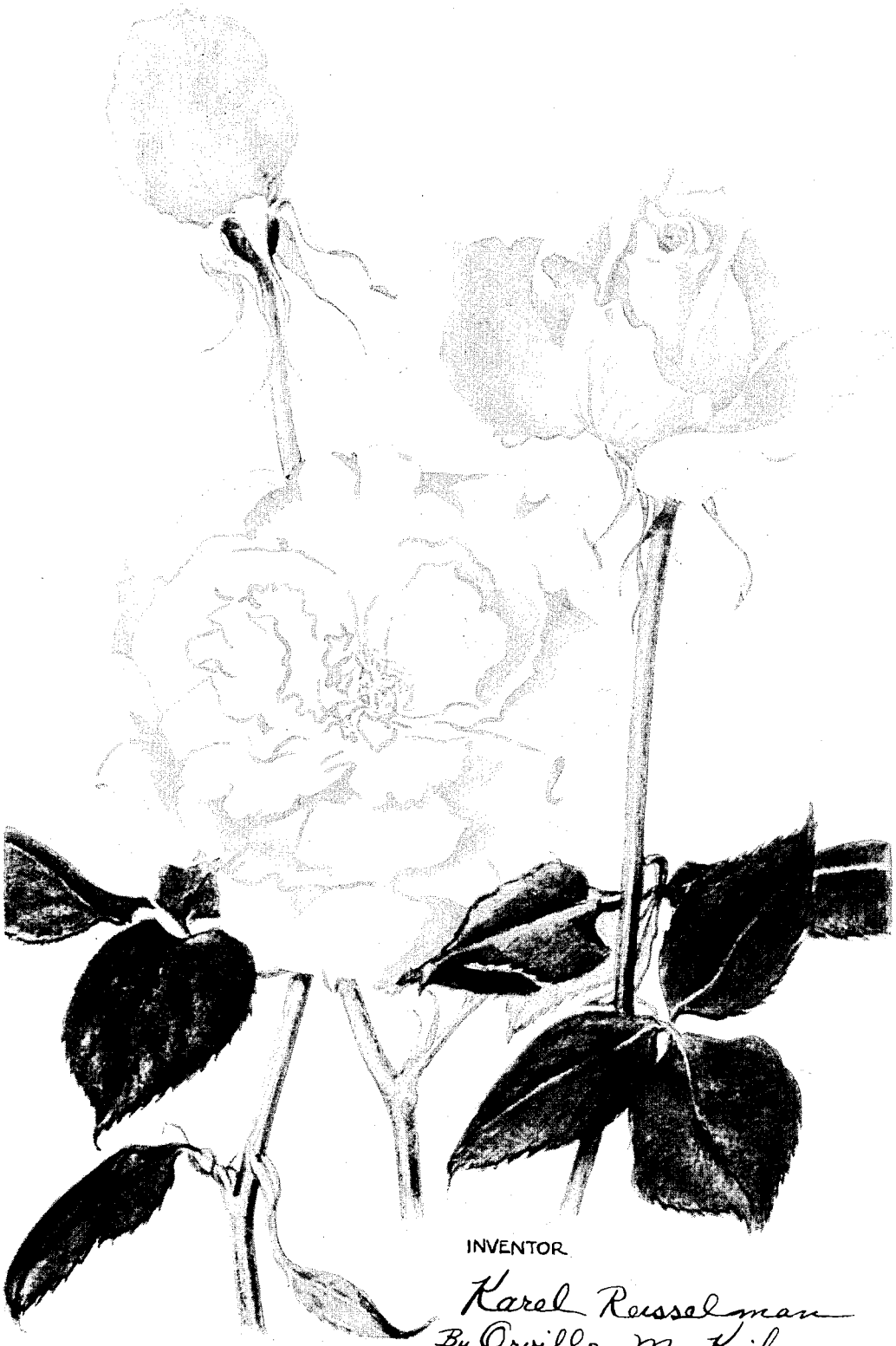
INVENTOR
Karel Riesselmann
By Orville M. Kile
PLANT PATENT AGENT Patented June 13, 1939

Plant Pat. 330

UNITED STATES PATENT OFFICE

330

ROSE

Karel Riesselmann, North Wales, Pa., assignor to The Florex Gardens, North Wales, Pa., an incorporated company of Pennsylvania Application November 23, 1938, Serial No. 242,111

1 Claim. (Cl. 47—61)

My discovery relates to improvements in pink hybrid tea roses. It is a sport of Better Times and was discovered as a particularly strong branch of a plant of this variety growing in my greenhouses. It is like its parent in growth and most other respects. Its principal distinguishing feature is the color of its blossom, which is considerably darker than that of its parent, and is much like that of the variety Hollywood. A small amount of reddish color on the foliage is also a noticeable distinguishing feature.

The accompanying illustration, in the original, shows three blossoms of this variety in various stages of opening, together with a portion of the stems and leaves.

A description of Better Times would, with few differences, describe my new variety, but I am also giving below some details of the description. Plate references are to Ridgway's Color Standards and Nomenclature.

*The plant*

Growth habits:

Upright bush; vigorous; clean; very healthy.

Foliage:

Abundant; smooth-surfaced; large.

*Leaves.*—Compound, with 3 to 5 leaflets.

*Leaflets.*—Elliptical, with sharp apex; serrations sharp; length twice that of width. Terminal leaflet unusually large.

*Color.*—Approximately Dark Dull Yellow-Green (Plate XXXII) on upper side. The under side has the appearance of Cedar Green (Plate VI) overcast with gray. Very little bronze or reddish cast is present.

*Rachis:*

Smooth; upper side grooved.

*Stipules:*

Clinging; medium length and width; points straight, long and sharp.

*Stems:*

Long and sturdy; smooth; Parrot Green (Plate VI).

*The flower*

Bud:

*Form.*—Pointed; slender.

*Size.*—Medium length, average being about 1½ inches.

*Color.*—Rose Color (Plate XII); almost uniformly spread but slightly darker at base of petal.

*Veining.*—Prominent.

Blossom:

Borne singly.

*Size.*—Medium, average being 4 inches across.

*Form.*—Center medium high, retaining its form until very old. Stamens usually remain covered by one or two petals which fold to form a sort of tent.

*Petalage.*—Double, with 20 to 25 petals in the month of September.

*Petals:*

*Substance.*—Thick; leathery.

*Shape.*—Outer petals almost round, with slightly fluted edges.

*Color.*—The general color effect is between Rose Color and Rose Red (Plate XII). However, the color lightens toward the base of the petal on the inside, where it meets a small aiglet of Empire Yellow (Plate IV). Upon aging, the color darkens. Occasional vertical streaks of white are visible when the flower is fully open.

*Fragrance.*—Pleasant and lasting; somewhat like that of the American Beauty rose.

*Persistence.*—Petals cling tenaciously.

*Lasting qualities.*—Unusually long lasting as a cut flower.

*Reproductive organs*

*Pistils.*—Numerous; bunched.

*Styles.*—White at bottom and red at top; considerably enlarged at top.

*Stigmas.*—Ecru or buff colored.

*Stamens.*—Fewer than pistils and surrounding same.

*Filaments.*—Pink.

*Anthers.*—Dark brown, edged with yellow.

Having thus disclosed my discovery, I claim:

A new and distinct variety of hybrid tea rose similar to Better Times in growth and form but characterized particularly in its blossoms of Rose Color to Rose Red, and its excellent lasting quality as a cut flower.

KAREL RIESSELMANN.